United States Patent
Eck et al.

(10) Patent No.: US 6,646,161 B1
(45) Date of Patent: Nov. 11, 2003

(54) METHOD FOR THE FRACTIONAL CONDENSATION OF A HOT GAS MIXTURE CONTAINING ACRYLIC ACID OR METHACRYLIC ACID AND HAVING A HIGH PROPORTION OF NON-CONDENSABLE CONSTITUENTS

(75) Inventors: Bernd Eck, Viernheim (DE); Otto Machhammer, Mannheim (DE); Theo Proll, Bad Dürkheim (DE); Volker Schliephake, Schifferstadt (DE); Joachim Thiel, Neustadt (DE); Klaus Bröllos, Seeheim-Jugenheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/508,077

(22) PCT Filed: Sep. 10, 1998

(86) PCT No.: PCT/EP98/05779
§ 371 (c)(1),
(2), (4) Date: Mar. 13, 2000

(87) PCT Pub. No.: WO99/14182
PCT Pub. Date: Mar. 25, 1999

(30) Foreign Application Priority Data

Sep. 12, 1997 (DE) .......................................... 197 40 253

(51) Int. Cl.[7] .......................... C07C 51/42; C07C 51/16

(52) U.S. Cl. .......................... 562/600; 562/545; 562/532

(58) Field of Search .................................. 562/545, 532, 562/600

(56) References Cited

U.S. PATENT DOCUMENTS

| | | | | | |
|---|---|---|---|---|---|
| 4,156,633 A | * | 5/1979 | Horlenko et al. | .............. | 203/93 |
| 4,599,144 A | * | 7/1986 | Baleiko et al. | ................ | 203/15 |
| 5,326,916 A | * | 7/1994 | Kobayashi | ................... | 568/492 |
| 5,426,221 A | * | 6/1995 | Willersinn | ................... | 562/600 |
| 5,684,188 A | * | 11/1997 | Hefner | ....................... | 562/532 |
| 5,770,021 A | * | 6/1998 | Hego et al. | .................... | 203/8 |

OTHER PUBLICATIONS

Schaap, Formation of stable bicyclic 1,2–Dioxetanes from the addition of single oxygen to p–dioxene and 1,3–dioxole, May 1971, Tetrahedron Letters, and P. 11757–60.*

* cited by examiner

Primary Examiner—Alan L. Rotman
Assistant Examiner—Taylor V. Oh
(74) Attorney, Agent, or Firm—Oblon, Spivak, McClelland, Maier & Neustadt, P.C.

(57) ABSTRACT

A process for the fractional condensation of a gas mixture which, in addition to acrylic acid or methacrylic acid, also contains at least one further condensable component and additionally a high proportion of one or more noncondensable components, wherein the gas mixture is passed through a column having separatory internals and the condensable components are condensed by cooling.

14 Claims, 1 Drawing Sheet

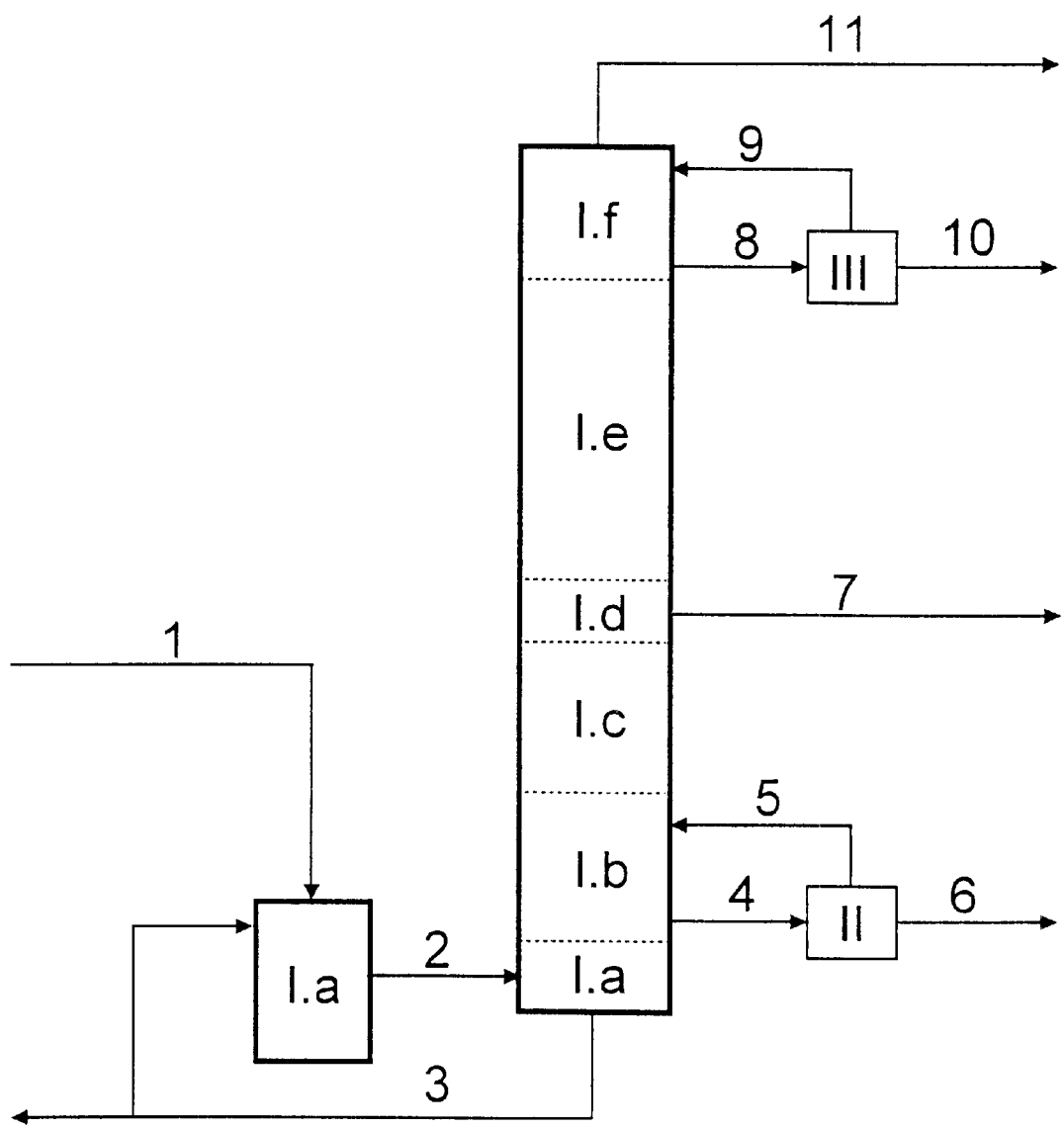

METHOD FOR THE FRACTIONAL CONDENSATION OF A HOT GAS MIXTURE CONTAINING ACRYLIC ACID OR METHACRYLIC ACID AND HAVING A HIGH PROPORTION OF NON-CONDENSABLE CONSTITUENTS

The present invention relates to a process for the fractional condensation of a hot gas mixture which contains at least two condensable components and a high proportion of noncondensable components.

Hot gas mixtures which, in addition to condensable components, contain a high proportion of noncondensable components are formed, for example, in the preparation of acrylic acid or methacrylic acid by gas-phase oxidation under heterogeneous catalysis. Here, for example, propene is reacted with molecular oxygen over solid catalysts at from 200 to 400° C. in one stage or two stages via acrolein (cf. for example DE-A-1 962 431, DE-A-2 943 707, DE-C-1 205 502, EP-A-0 257 565, EP-A-0 253 409, DE-A-2 251 364, EP-A-0 117 146, GB-B-1 450 986 and EP-A-0 293 224). Multicomponent oxidic catalysts, for example based on oxides of the elements molybdenum, bismuth and iron (in stage I) or molybdenum and vanadium (in stage II) are used. The hot reaction gas mixture formed contains, in addition to the "condensable" acrylic acid or the "condensable" methacrylic acid and condensable byproducts, a high proportion of noncondensable components, such as nitrogen or oxygen.

Numerous processes are known for isolating the acrylic acid. Thus, DE-C-2 136 396 discloses isolating the acrylic acid from the reaction gases obtained in the catalytic gas-phase oxidation by countercurrent absorption using a mixture of about 75% by weight of diphenyl ether and about 25% by weight of biphenyl. DE-A-2 449 780 describes the cooling of the hot reaction gas by partial evaporation of the solvent in a direct condenser (quench apparatus) before the countercurrent absorption. In addition to this absorption of the acrylic acid-containing reaction product into a high-boiling solvent mixture, other processes envisage a total condensation of acrylic acid and of the water of reaction also formed in the catalytic oxidation. The result is an aqueous acrylic acid solution which can be further worked up by distillation with an azeotropic agent (cf. for example DE-C-3 429 391 and JP-A-1 124 766) or by an extraction method (cf. for example DE-A-2 164 767 and JP-A-5 81 40-039). In EP-A-0 551 111, the acrylic acid-containing mixture prepared by means of gas-phase oxidation is brought into contact with water in an absorption tower, and the aqueous solution obtained is distilled in the presence of a solvent which forms an azeotropic mixture with polar low boilers, such as water or acetic acid. Furthermore, DE-C-2 323 328 discloses the isolation of acrylic acid from an aqueous butanol/acrylic acid esterification waste liquor by extraction with a special mixture of organic solvents. The disadvantage of the processes described here is that the extraction or absorption requires an organic solvent which has to be separated off again in a further process stage, such as rectification, with high thermal stress.

It is an object of the present invention to provide a process for separating a gas mixture formed in the catalytic gas-phase oxidation to give acrylic acid or methacrylic acid and having a high proportion of noncondensable components, so that acrylic acid or methacrylic acid is obtained in high purity and very few processes stages are required.

We have found that this object is achieved by a process for the fractional condensation of a gas mixture which, in addition to acrylic acid or methacrylic acid, also contains at least one further condensable component and additionally a high proportion of one or more noncondensable components. In the novel process for the fractional condensation, the gas mixture is passed through a column having separatory internals and the condensable components are condensed by cooling.

According to the invention, a process for the preparation of acrylic acid or methacrylic acid is also provided. Said process is based on the catalytic gas-phase oxidation of $C_3$-/$C_4$-alkanes, -alkenes, -alkanols and/or -alkanals and/or intermediates thereof with formation of a crude product which, in addition to acrylic acid or methacrylic acid, also contains at least one byproduct and/or at least one unconverted starting material. In the novel preparation process, the gaseous crude product is worked up by the above novel process for fractional condensation.

In a preferred embodiment, the hot gas mixture contains a high boiler fraction, medium boiler fraction and low boiler fraction, each of which in turn contains one or more components, as is the case, for example, with the hot reaction product gas mixture formed in the preparation of acrylic acid by catalytic gas-phase oxidation. Further preferred embodiments of the invention are evident from the following description and from the Example. The invention furthermore relates to the use of a column having separatory internals for the fractional condensation of hot gas mixtures containing a high proportion of noncondensable components.

The only FIGURE schematically shows a column which is preferably used for carrying out the novel process.

The columns which can be used for the novel process are not subject to any particular restriction. In principle, all columns having separatory internals are suitable. Suitable column internals are all conventional internals, in particular trays, stacked packings and/or dumped packings. Among the trays, bubble trays, sieve trays, valve trays and/or dual-flow trays are preferred. The column comprises at least one cooling apparatus. All heat exchangers in which the heat liberated in the condensation is removed indirectly (externally) are suitable for this purpose. All conventional apparatuses may be used for this purpose, tube-bundle heat exchangers, plate-type heat exchangers and air coolers being preferred. Suitable cooling media are accordingly air in the case of an air cooler and cooling liquids, in particular water, in the case of other cooling apparatuses. If only one cooling apparatus is provided, it is installed at the top of the column in which the low boiler fraction is condensed. A person skilled in the art can readily determine the number of cooling apparatuses required, depending on the desired purity of the condensed fractions and hence of the components, the purity of the condensed components essentially being determined by the installed separation efficiency of the column, i.e. the column height and the energy introduced via the gas mixture to be condensed. When a plurality of cooling apparatuses are present, they are expediently installed in different sections of the column. For example, in the case of the hot gas mixture which, in addition to the high proportion of noncondensable components, contains a high boiler fraction, medium boiler fraction and low boiler fraction, a cooling apparatus can be provided in the lower section of the column for condensing the high boiler fraction and a cooling apparatus can be provided at the top of the column for condensing the low boiler fraction. The condensed fractions are removed from the respective sections of the column via side take-offs. Depending on the number of components in the high boiler fraction, medium boiler fraction and low boiler fraction, a plurality of side take-offs may also be present in each case. The fractions removed via the side take-offs can then be subjected to further purification stages, for example distillative or extractive separation processes or a crystallization, depending on the desired purity of the components. In a preferred embodiment of the invention, a high boiler take-off, a low boiler take-off and 0, 1 or 2 medium-boiler take-offs are provided. The pressure present in the column depends on the amount of noncondensable components and is preferably 0.5–5, in particular 0.8–3, bar absolute pressure. The exact operating conditions for the column, such as temperature and pressure, connection and arrangement of the cooling apparatus(es), arrangement of the side take-offs for removing the desired fractions, choice of column height and of column diameter, number and spacing of the separatory internals/trays in the column or type of separatory column internals, can be determined by a person skilled in the art by conventional experiments depending on the separation task.

Gas mixtures which may be used are all hot gas mixtures which contain at least two condensable components and a high proportion of at least one noncondensable component and do not exhibit any pronounced formation of an azeotropic mixture, i.e. azeotropic mixtures are also suitable when the composition of the azeotropic mixture is shifted very far to one side. According to the invention, the term "condensable components" covers all components or compounds whose boiling point is not lower than −40° C. at atmospheric pressure (1 bar), preferably not lower than −30° C. at atmospheric pressure (1 bar), in particular not lower than −20° C. at atmospheric pressure (1 bar). Advantageously, the temperature of the hot gas mixture to be condensed is from 20 to 450° C., in particular from 100 to 350° C., most preferably from 150 to 300° C. The proportion of noncondensable component or components is advantageously from 20 to 100, in particular from 50 to 95, most preferably from 70 to 90, % by weight, based in each case on 100% by weight of hot gas mixture. In a preferred embodiment of the invention, the gas mixture contains, in addition to noncondensable component or components, a high boiler fraction, medium boiler fraction and low boiler fraction, each of which in turn contains one or more components. The terms high boiler fractions and low boiler fractions are based here on the desired product which appears in the medium boiler fraction and denote the fractions which have a boiling point or boiling range higher or lower, respectively, than the medium boiler fraction, said fraction differing by at least 5 to 10° C. from the boiling range/boiling point of the medium boiler fraction.

In a preferred embodiment, the hot gas mixture is cooled directly or indirectly (externally) before the condensation. This can be effected by indirect cooling, for example by means of a gas cooler, but also by direct cooling with a refrigerant high-boiling assistant, for example high-boiling hydrocarbons, or preferably with the high boiler fraction condensed from the gas mixture. In the case of the assistant, however, a disadvantage is that it must be worked up again. In terms of apparatus, the cooling can be carried out separately from the column in a separate apparatus, for example in a gas cooler, a quench or a flash vessel, or integrated in the bottom of the column (with or without column internals). During the cooling, the hot gas mixture is cooled to 50 to 300° C., in particular to 70 to 200° C., below the boiling point of the highest-boiling component in each case.

A particularly suitable hot gas mixture is the reaction gas mixture as formed in the catalytic gas-phase oxidation of $C_3$- or $C_4$-alkanes, -alkenes, -alkanols and/or -alkanals and/or intermediates thereof to give acrylic acid or methacrylic acid by known processes. Propene, propane, acrolein, tert-butanol, isobutene, isobutane, isobutyraldehyde, methacrolein, isobutyric acid or methyl tert-butyl ether is particularly advantageously used. However, other suitable starting compounds are those from which the actual $C_3/C_4$ starting compound is formed as an intermediate during the gas-phase oxidation itself An example is isobutyric acid or methyl tert-butyl ether for the preparation of methacrylic acid. Thus, a gas mixture from the catalytic gas-phase oxidation of $C_3$-/$C_4$-alkanes, -alkenes, -alkanols and/or -alkanals and/or intermediates thereof to give acrylic acid or to give methacrylic acid is thus preferably present as a crude product for the condensation. Both acrylic acid and methacrylic acid can be prepared directly from propane and isobutane, respectively. When propane is used as a starting material, it can be converted into a propene/propane mixture by catalytic oxydehydrogenation (for example according to U.S. Pat. No. 5,510,558), homogeneous oxydehydrogenation (for example according to CN-A-1 105 352) or catalytic dehydrogenation (for example according to EP-A-0 253 409) by known processes. Suitable propene/propane mixtures are also refinery propene (70% of propene and 30% of propane) and cracker propene (95% of propene and 5% of propane). When a propene/propane mixture is used for the preparation of acrylic acid, propane acts as a diluent gas and/or reactant. As in the case of propane, isobutane too can act as a reactant, and both can be converted directly into acrylic acid or methacrylic acid, for example according to EP-B-0 608 838. In the preparation of acrylic acid or methacrylic acid, as a rule the starting gases are diluted with inert gases, such as nitrogen, $CO_2$, saturated $C_1$–$C_6$-hydrocarbons and/or steam, passed as a mixture with oxygen at elevated temperatures (usually from 200 to 450° C.) and, if required, superatmospheric pressure over transition metal mixed oxide catalysts (containing, for example, Mo, V, W and/or Fe) and oxidized to acrylic acid or methacrylic acid (cf. for example DE-A-4 405 059, EP-A-0 253 409, EP-A-0 092 097 and DE-A-4 431 949). These reactions are carried out, for example, in one or more stages. Particularly suitable processes for the preparation of methacrylic acid are those which start from methacrolein, in particular if the methacrolein is produced by gas-phase catalytic oxidation of tert-butanol, isobutane or isobutene or by reaction of formaldehyde with propionaldehyde according to EP-B-0 092 097 and EP-B-0 058 927. In addition to the desired acid, the resulting reaction gas mixture contains byproducts such as unconverted acrolein or methacrolein and/or propene and/or isobutene, steam, carbon monoxide, carbon dioxide, nitrogen, oxygen, acetic acid, propionic acid, formaldehyde, further aldehydes and maleic anhydride. Usually, the reaction gas mixture contains from 1 to 30% by weight of acrylic acid or methacrylic acid, from 0.05 to 1% by weight of propene or isobutene and from 0.05 to 1% by weight of acrolein or methacrolein, from 0.05 to 10% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes, from 0.01 to 0.5% by weight of maleic anhydride and from 20 to 98, preferably 50–90, % by weight of inert diluent gases, based in each case on the total reaction gas mixture. In particular, saturated $C_1$–$C_6$-hydrocarbons, such as from 0 to 90% by weight of methane and/or propane, in addition to from 1 to 30% by weight of steam, from 0.05 to 15% by weight of oxides of carbon and from 0 to 90% by weight of nitrogen, based in each case on 100% by weight of diluent gas, are present as inert diluent gases. In addition to the desired component acrylic acid or methacrylic acid, which condenses as a medium boiler fraction, such a gas mixture therefore contains further compounds in the high boiler and low boiler range. Expediently, the fractional condensation is then carried out by providing two cooling apparatuses in the column, one on the lower region of the column for condensing the high-boiling components and one in the upper region of the column for condensing the low boiler fraction.

Advantageously, the process is carried out in the presence of a high boiler fraction, a medium boiler fraction, a low boiler fraction and noncondensable component(s), as shown in the FIGURE and as described below, it being possible to divide the column into various sections in which different process engineering problems are solved. Here, the reference symbols in the FIGURE refer to the individual sections in the column (I.a to I.f) or separate sections/apparatuses of the column (I.a), feed lines and exit lines (1–11) and the cooling circulations II and III.

I.a Bottom Region

Cooling of the Hot Gas Mixture

In the bottom region I.a, the hot gas mixture is passed in and cooled. This can be effected by indirect cooling, for example by means of a heat exchanger, or direct cooling with, as a cooling medium, high boiler fraction condensed in the next section of the column. Instead of being effected in the bottom region of the column, the cooling can also be carried out analogously, separately from the column, in a separate apparatus I.a, as shown in the FIGURE. In this case, the hot gas mixture to be condensed, from line 1, is cooled in a quench or prequench I.a and fed via line 2 to the bottom region I.a of the column. The cooling medium (condensed high boiler fraction) for cooling the hot gas mixture is recycled to the quench or prequench via line 3.

If the cooling is carried out using a high-boiling assistant or using the high boiler fraction from region I.b., a part of the stream, usually less than 1% by weight, based on 100% by weight of condensate in the side take-off, can be removed from the process.

I.b Cooling Circulation II

Condensation of the High Boiler Fraction

In column section I.b, the heat of condensation is removed externally via cooling circulation II by means of a heat exchanger with, for example, water as coolant, by removing condensed high boiler fraction from the column via line 4, cooling said fraction and recycling a part of the cooled, condensed high boiler fraction via line 5 to the column, while the other part, usually less than 1% by weight, based on 100% by weight of condensate in the side take-off, is removed via line 6. The recycled, condensed high boiler fraction is fed countercurrent to the ascending gas. Depending on the separation task, it is also possible to combine (not shown) sections I.a and I.b of the column, i.e. the cooling of the reaction gas and the condensation of a high boiler fraction, in terms of apparatus so that said processes are carried out simultaneously. It is also possible, instead of the external cooling circulation II, to provide direct cooling (not shown) where high-boiling assistant is injected for cooling and is once again circulated or is worked up externally.

I.c Cooling Circulation II→Side Take-off

High Boiler Concentration

In column section I.c, between column section I.b (cooling circulation II) and I.d (side take-off), a distillative concentration and condensation of the high boiler fraction from the gas stream fed countercurrent in an upward direction is effected toward cooling circulation II.

I.d Side Take-off

Taking off the Medium Boiler Fraction

Desired components, such as acrylic acid or methacrylic acid, are removed via side take-off 7 in column section I.d. In the limiting case of a one-stage condensation, the medium boiler fraction is condensed, in the region of the side take-off 7, from the gas mixture fed countercurrent in an upward direction.

I.e Side Take-off→Cooling Circulation III

Medium Boiler Concentration

In column section I.e, between column section I.d (side take-off 7) and I.f (cooling circulation III), the distillative concentration of the medium boiler fraction from the, gas stream fed upward in the gas mixture is effected, the medium boiler fraction being concentrated toward the side take-off (region I.d). It is also possible to combine (not shown) sections I.d and I.e of the column in terms of apparatus to give one section. In this case, a collecting tray is expediently installed in section I.d of the column in order to remove the liquid from the column.

I.f Cooling Circulation III

Condensation of the Low Boiler Fraction

The condensation of the low boiler fraction from the gas stream fed countercurrent in an upward direction is carried out in column section I.f of the external cooling circulation III. Analogously to cooling circulation II, the heat of condensation is removed externally via cooling circulation III by means of a heat exchanger with, for example, water as coolant, by removing condensed low boiler fraction via line 8, cooling said fraction and recycling a part of the cooled, condensed low boiler fraction via line 9 to the column, while the other part is removed via line 10. The uncondensed gases are taken off at the top of the column via line 11, it being possible, if necessary, also to superheat the gas stream to avoid further condensation in the vapor pipe.

The column shown schematically in the FIGURE is particularly suitable for the fractional condensation of an above-mentioned reaction gas mixture as formed in the catalytic gas-phase oxidation to give acrylic acid or methacrylic acid. In this case, a stabilizer, in particular phenothiazine or another stabilizer disclosed in EP-A-0 765 856, is advantageously added to the column at one or more points which can be readily determined by a person skilled in the art, in order to avoid polymerization. The desired product, the acrylic acid or methacrylic acid, is removed from the column via side take-off 7 in a high purity of more than 95, in particular more than 97, % by weight, based in each case on the condensate removed in the side take-off. The non-condensable components, which are preferably nitrogen, carbon monoxide, carbon dioxide, oxygen, methane, propane and propene, are removed at the top of the column via line 11. The high boiler fraction which has condensed in section I.b and contains predominantly maleic anhydride, benzoic acid, stabilizers, such as phenothiazine or other stabilizers disclosed in EP-A-0 765 856, and monomeric and oligomeric acrylic acid is removed via line 6, while the condensed low boiler fraction, which predominantly contains water, acetic acid and formaldehyde, is removed via line 10.

In contrast to the processes to date for isolating acrylic acid, which require the use of an absorbent or extracting agent, according to the invention acrylic acid or methacrylic acid can be isolated in high purity by passing hot reaction gases from the catalytic gas-phase oxidation into an absorption column from the bottom and allowing said gases to ascend into themselves without passing an external absorbent countercurrent. The ascending gases cool, and the condensable components condense and form, so to speak, a descending "internal absorbent". The novel process thus permits the isolation of acrylic acid or methacrylic acid in high purity without an external absorbent or extracting agent. Furthermore, the process permits optimum utilization of the heat energy which is contained in the hot reaction gases from the catalytic gas-phase oxidation. Moreover, the noncondensable components removed via the top can be recycled as diluent gas or circulation gas to the stage for the preparation of the acrylic acid or methacrylic acid.

The novel process permits, in only one process stage, not only separation of a hot gas mixture into a condensable portion and a noncondensable portion, but simultaneously separation of the condensable portion into fractions boiling at various boiling points or boiling ranges and hence high purity of the various components. As stated above, condensed components form, so to speak, a descending "internal absorbent", and it is for this reason that the novel process may be regarded in simplified terms as an advantageous combination of rectification and absorption. It is particularly surprising that this high purity of the components is possible without the use of an assistant. The novel process optimally utilizes the heat energy of gas mixtures from reactions in which hot gas mixtures form. The novel process differs from conventional distillation, rectification and condensation processes in that a high proportion of noncondensable components is present. Usually, the proportion of noncondensable components is less than 5% in the above-mentioned conventional processes. The novel process thus permits a particularly economical separation of a hot gas mixture with a high proportion of noncondensable components into its condensable components in a single process stage. That the desired components can be obtained in high purity is particularly advantageous.

The invention is illustrated below with reference to the following Example, which represents a preferred embodiment of the invention.

EXAMPLE

A mixture having the following composition (Table 1) and a temperature of 270° C. was obtained from a catalytic gas-phase oxidation to acrylic acid:

TABLE 1

| Component | Concentration, % by weight |
|---|---|
| Water | 4.4 |
| Formaldehyde | 0.2 |
| Acetic acid | 0.4 |
| Acrylic acid | 10.1 |
| Maleic anhydride | 0.07 |
| Benzoic acid | 0.02 |
| Acrolein | 0.1 |
| Phthalic anhydride | 0.01 |
| Propionic acid | 0.002 |
| Maleic acid | 0.0 |
| Allyl acrylate | 0.001 |
| Benzaldehyde | 0.001 |
| Furfural | 0.001 |
| Phenothiazine | 0.0 |
| Nitrogen | Remainder (76.545) |
| Oxygen | 3.6 |
| Carbon monoxide | 0.75 |
| Carbon dioxide | 2.6 |
| Propene | 0.5 |
| Propane | 0.7 |

The mixture (3040 g/h) was introduced from below into a column which schematically is formed essentially like the column shown in the FIGURE. A column having bubble trays was used. The column was 2.6 m high and had a diameter of 8 cm. The number of trays was 27. The temperature at the bottom of the column was 120° C. The heat of condensation was removed via heat exchangers and trays 1 and 27. Phenothiazine was added continuously as a stabilizer at the top of the column.

1 g/h of a high boiler fraction having the composition stated in Table 2 was removed at 120° C. from the bottom of the column via a side take-off:

TABLE 2

| Component | Concentration, % by weight |
|---|---|
| Water | 0.6 |
| Formaldehyde | 0.002 |
| Acetic acid | 0.403 |
| Acrylic acid | 40 |
| Maleic anhydride | 0.9 |
| Benzoic acid | 9.0 |
| Acrolein | 0.006 |
| Phthalic anhydride | 3.6 |
| Propionic acid | 0.008 |
| Maleic acid | 0 |
| Allyl acrylate | 0.002 |
| Benzaldehyde | 0.006 |
| Furfural | 0.009 |
| Phenothiazine | Remainder (45.464) |
| Nitrogen | 0 |
| Oxygen | 0 |
| Carbon monoxide | 0 |
| Carbon dioxide | 0 |
| Propene | 0 |
| Propane | 0 |

350 g/h of the following medium boiler fraction (Table 3) were removed at 93° C. from tray 3 of the column via a side take-off:

TABLE 3

| Component | Concentration, % by weight |
|---|---|
| Water | 1.1 |
| Formaldehyde | 0.004 |
| Acetic acid | 1.0 |
| Acrylic acid | Remainder (96.914) |
| Maleic anhydride | 0.6 |
| Benzoic acid | 0.2 |
| Acrolein | 0.008 |
| Phthalic anhydride | 0.1 |
| Propionic acid | 0.02 |
| Maleic acid | 0 |
| Allyl acrylate | 0.01 |
| Benzaldehyde | 0.004 |
| Furfural | 0.01 |
| Phenothiazine | 0.03 |
| Nitrogen | 0 |
| Oxygen | 0 |
| Carbon monoxide | 0 |
| Carbon dioxide | 0 |
| Propene | 0 |
| Propane | 0 |

90 g/h of the following low boiler fraction (Table 4) were removed at 34° C. from tray 27:

TABLE 4

| Component | Concentration, % by weight |
|---|---|
| Water | Remainder (87.69) |
| Formaldehyde | 0.08 |
| Acetic acid | 8.2 |
| Acrylic acid | 4.0 |
| Maleic anhydride | 0 |

TABLE 4-continued

| Component | Concentration, % by weight |
|---|---|
| Benzoic acid | 0 |
| Acrolein | 0.03 |
| Phthalic anhydride | 0 |
| Propionic acid | 0 |
| Maleic acid | 0 |
| Allyl acrylate | 0 |
| Benzaldehyde | 0 |
| Furfural | 0 |
| Phenothiazine | 0 |
| Nitrogen | 0 |
| Oxygen | 0 |
| Carbon monoxide | 0 |
| Carbon dioxide | 0 |
| Propene | 0 |
| Propane | 0 |

The noncondensable components (exit gas) were removed via the top. At 2640 g/h and 25° C., their composition was as follows:

TABLE 5

| Component | Concentration, % by weight |
|---|---|
| Water | 2.0 |
| Formaldehyde | 0.2 |
| Acetic acid | 0.09 |
| Acrylic acid | 0.03 |
| Maleic anhydride | 0 |
| Benzoic acid | 0 |
| Acrolein | 0.1 |
| Phthalic anhydride | 0 |
| Propionic acid | 0 |
| Maleic acid | 0 |
| Allyl acrylate | 0 |
| Benzaldehyde | 0 |
| Furfural | 0 |
| Phenothiazine | 0 |
| Nitrogen | Remainder (88.18) |
| Oxygen | 4.1 |
| Carbon monoxide | 0.9 |
| Carbon dioxide | 3.0 |
| Propene | 0.6 |
| Propane | 0.8 |

As is evident from a comparison of Table 3 with the other tables, acrylic acid of high purity and good separation of the further components are obtained by the use of a column for the condensation.

We claim:

1. A process for the fractional condensation of a gas mixture comprising acrylic acid or methacrylic acid, at least one further condensable component, and additionally a high proportion of one or more noncondensable components, the process comprising passing the gas mixture through a column having separatory internals, condensing the condensable components by cooling, and removing acrylic acid or methacrylic acid having a purity of more than 95% by weight from the column.

2. The process as claimed in claim 1, wherein the gas mixture is a crude product formed by catalytic gas-phase oxidation of $C_3$-/$C_4$-alkanes, -alkenes, -alkanols and/or -alkanals and/or at least one intermediate thereof selected from the group consisting of isobutyric acid and methyl tert-butyl ether to give acrylic acid or methacrylic acid.

3. The process as claimed in claim 1, wherein the gas mixture is cooled before the condensation.

4. The process as claimed in claim 1, wherein the gas mixture is a hot gas mixture having a high boiler fraction comprising one or more compounds selected from the group consisting of maleic anhydride, benzoic acid, stabilizers, monomeric and oligomeric acrylic acid, a medium boiler fraction comprising acrylic or methacrylic acid, and a low boiler fraction comprising one or more compounds selected from the group consisting of water, acetic acid, and formaldehyde, and the hot gas mixture is condensed.

5. A process as claimed in claim 4, wherein each of the high boiler, medium boiler and low boiler fractions contains one or more components.

6. The process as claimed in claim 1, wherein the gas mixture is a hot gas mixture comprising from 20 to 98% by weight of noncondensable components selected from the group consisting of nitrogen, oxygen, carbon monoxide, methane, propane, and propene, based on 100% by weight of the gas mixture, and the hot gas mixture is condensed.

7. The process as claimed in claim 1, wherein the gas mixture is a hot gas mixture at from 100 to 350° C., and the hot gas mixture is condensed.

8. The process as claimed in claim 1, wherein a column having one or more cooling apparatuses is used.

9. The process as claimed in claim 1, wherein the separatory column internals are selected from the group consisting of stacked packings, dumped packings, trays, and combinations thereof.

10. A process for the preparation of acrylic acid or methacrylic acid by catalytic gas-phase oxidation of a starting material comprising at least one compound selected from the group consisting of $C_3$-/$C_4$-alkanes, -alkenes, -alkanols and/or -alkanals and/or at least one intermediate thereof selected from the group consisting of isobutyric acid and methyl tert-butyl ether with formation of a gaseous crude product comprising acrylic acid or methacrylic acid, at least one byproduct selected from the group consisting of acrolein, methacrolein, propene, isobutene, steam, carbon monoxide, carbon dioxide, nitrogen, oxygen, acetic acid, propionic acid, formaldehyde, aldehydes other than formaldehyde, and maleic anhydride, and/or at least one unconverted starting material, wherein the gaseous crude product is condensed by a process as claimed in claim 1.

11. The process as claimed in claim 1, wherein the gas mixture is cooled to 50 to 300° C.

12. The process as claimed in claim 1, wherein the gas mixture is cooled to 70 to 200° C.

13. The process as claimed in claim 1, wherein the gas mixture comprises 1 to 30% by weight of acrylic acid or methacrylic acid, and 0.05 to 1% by weight acrolein or methacrolein.

14. A process for the purification of acrylic or methacrylic acid comprising:
cooling a hot gas mixture comprising acrylic or methacrylic acid, at least one additional condensable component selected from the group consisting of water, acetic acid, formaldehyde, maleic anhydride, benzoic acid, acrolein, phthalic anhydride, propionic acid, maleic acid, allyl acrylate, benzaldehyde, fufural, and phenothiazine, and 20–98% by weight of a noncondensable component selected from the group consisting of nitrogen, oxygen, carbon monoxide, carbon dioxide, methane, propane and propene;
injecting the cooled gas into a column comprising separatory internals at a lower portion of the column;
removing the heat of condensation from the lower portion of the column with a heat exchanger, thereby removing a condensed high boiler fraction comprising one or more compounds selected from the group consisting of maleic anhydride, benzoic acid, stabilizers, monomeric and oligomeric acrylic acid from the column;

recirculating a portion of the condensed high boiler fraction into the column;

removing a medium boiler fraction comprising acrylic acid or methacrylic acid at a middle portion of the column;

removing the heat of condensation from an upper portion of the column with a heat exchanger, thereby removing a condensed low boiler fraction comprising one or more compounds selected from the group consisting of water, acetic acid, and formaldehyde from the column;

recirculating a portion of the condensed low boiler fraction into the column;

removing uncondensed gases from the upper portion of the column.

\* \* \* \* \*